United States Patent [19]

Corfield et al.

[11] Patent Number: 4,522,840

[45] Date of Patent: Jun. 11, 1985

[54] MANUFACTURE OF HIGHLIGHTED INTAGLIATED ARTICLES

[75] Inventors: Brian L. Corfield, Macclesfield; Raymond C. Rowe, Congleton, both of England

[73] Assignee: Imperial Chemical Industries PLC, London, England

[21] Appl. No.: 499,400

[22] Filed: May 31, 1983

[30] Foreign Application Priority Data

Jun. 10, 1982 [GB] United Kingdom ............... 8216815

[51] Int. Cl.$^3$ .............................................. A61K 9/00
[52] U.S. Cl. .......................................... 427/3; 424/31
[58] Field of Search ............................................. 427/3

[56] References Cited

FOREIGN PATENT DOCUMENTS 0060023 9/1982 European Pat. Off. .
7001076 8/1967 Japan ................................... 427/3

Primary Examiner—Sam Silverberg
Attorney, Agent, or Firm—Cushman, Darby & Cushman

[57] ABSTRACT

Process for manufacturing colored solid articles, e.g. pharmaceutical tablets, bearing at least one highlighted intagliation, which comprises (1) either (A) applying to said articles a film coating suspension comprising at least one defined optically anisotropic substance and at least one film coating agent, or (B) applying to said articles a suspension comprising at least one defined optically anisotropic substance but no film coating agent, and then (2) spraying the resulting articles with a solvent, and in which both of the steps (1) and (2) are carried out in a conventional film coating apparatus.

10 Claims, No Drawings

MANUFACTURE OF HIGHLIGHTED INTAGLIATED ARTICLES

This invention relates to an improved process for manufacturing intagliated articles in which the intagliations are highlighted.

In our European patent application No. 82300586.3 (Publication No. 60023 A1) there is described and claimed inter alia a process (hereinafter referred to generally as Process A) for the manufacture of coloured solid articles, for example medicinal tablets, bearing at least one highlighted intagliation, which comprises applying to coloured (i.e. non-white) intagliated articles a film coating suspension comprising at least one optically anisotropic substance having a minimum refractive index not greater than 2.00 and at least one film coating agent, the process being carried out in a conventional film coating apparatus in such a way that a rubbing action takes place between the articles being coated.

In United Kingdom patent application No. 8216816, there is described inter alia a process (hereinafter referred to generally as Process B) for the manufacture of coloured solid articles, for example medicinal tablets, bearing at least one highlighted intagliation, which comprises applying to coloured intagliated articles a suspension comprising at least one optically anisotropic substance having a minimum refractive index not greater than 2.00, but no film coating agent, in a suitable liquid, the process being carried out in a conventional film coating apparatus in such a way that a rubbing action takes place between the articles being coated.

It is to be understood that in this specification the expression "intagliated article" means a solid article, for example a tablet, which has at least one figure, mark or notation, or any combination thereof, cut into or formed in the surface of the article by a compression punching, incision or engraving procedure, or by any other procedure which produces a like effect. Furthermore, in this specification the expression "optically anisotropic substance" means a substance which exhibits different refractive indices in different directions.

In the highlighted products of the abovementioned Processes A and B there is a distinct contrast between the intagliation(s) and the remainder of the article. However, we have found that on occasions the said products have a slightly dusty appearance which tends to reduce the contrast between the intagliation(s) and the remainder of the article. This is somewhat more prevalent when the highlighting process is carried out on a fairly large scale in a relatively large coating machine, for example a 60 inch Accela-Cota (obtainable from Manesty Machines PLC, Speke, Liverpool 24, England). We have now made the surprising discovery, and herein lies the basis of this invention, that highlighted products of superior appearance, in which there is better contrast between the intagliation(s) and the remainder of the article, are obtained if a spray procedure is employed after the highlighting step.

According to the invention there is provided a process for the manufacture of coloured solid articles bearing at least one highlighted intagliation, which comprises:

(1) either (A) applying to coloured intagliated articles, which themselves may be uncoated or film coated, a film coating suspension comprising at least one optically anisotropic substance having a minimum refractive index not greater than 2.00 and at least one film coating agent, the application being carried out in a conventional film coating apparatus in such a way that a rubbing action takes place between the articles being coated;

or (B) applying to coloured intagliated articles, which themselves may be uncoated or film coated, a suspension comprising at least one optically anisotropic substance having a minimum refractive index not greater than 2.00, but no film coating agent, and the application being carried out in a conventional film coating apparatus in such a way that a rubbing action takes place between the articles being coated;

and characterised in that:

(2) the resulting coloured solid articles bearing at least one highlighted intagliation are sprayed with a solvent in a conventional film coating apparatus in such a way that a rubbing action takes place between the said articles.

The process of this invention is capable of wide application. Thus, for example, it can be used in the pharmaceutical or veterinary field, for example in the manufacture of pharmaceutical or veterinary unit dosage forms, for example pharmaceutical tablets or veterinary tablets (also known as boluses), bearing at least one highlighted intagliation, or in the sugar confectionery field, for example in the manufacture of highlighted pieces of sugar confectionery, for example sweets or candy, having approximately the same dimensions as a pharmaceutical tablet.

Process A can be summarised as follows:

(1) the articles used as the starting material are coloured intagliated articles of the appropriate dimensions, for example coloured intagliated pharmaceutical tablets;

(2) there is applied to the coloured intagliated articles a film coating suspension (hereinafter "the highlighting coating suspension") comprising at least one optically anisotropic substance having a minimum refractive index not greater than 2.00, and at least one film coating agent;

(3) the highlighting coating suspension is applied to the coloured intagliated articles in conventional manner in a conventional film coating apparatus in such a way that a rubbing action takes place between the articles being coated.

The coloured intagliated articles used as the starting material in Process A may be uncoated or they may be film coated. In the latter case the film coat may comprise any known film coating agent, for example a cellulose ether, for example hydroxypropyl methylcellulose or ethylcellulose, or cellulose acetate, shellac or an acrylic resin, or a mixture thereof. It may also contain one or more known film coating adjuvants, for example a plasticiser, for example glycerol, and/or a surface active agent and/or a wax. The film coat is applied in conventional manner in a conventional film coating apparatus, using either an organic solvent-based process, for example a process involving a mixture of methylene dichloride and methanol, or an aqueous process. The film coating apparatus may, for example, be a coating pan, or a coating drum, for example a side-vented perforated drum coating machine, or a so-called Wurster coating apparatus (a fluidized-bed coating apparatus).

The colour which characterises the said coloured intagliated articles used in Process A may be present throughout the articles or it may be applied to the surface thereof. Thus, for example, a colouring agent may be applied in the form of a colouring film coating solution or suspension to the surface of white articles. Any colouring agent which is approved for the purpose in question, for example pharmaceutical purposes, may be used, for example iron oxide (red, yellow or black), carmine, a natural dye, for example turmeric or betacarotene, a water-soluble dye, for example tartrazine, or an aluminium lake of a water-soluble dye, optionally in admixture with at least one opaque white pigment, for example titanium dioxide.

The optically anisotropic substance is used in the form of a powder. As suitable optically anisotropic substances there may be mentioned, for example, white optically anisotropic substances, for example known transparent white pigments (also known as "extender" or "inert" white pigments), for example aluminium hydroxide, china clay (kaolin), talc, calcium carbonate or barium carbonate. Other suitable optically anisotropic substances are magnesium carbonate (light or heavy form), cane sugar (sucrose), lactose or tartaric acid. Alternatively, in the case of a medicinal tablet or a bolus the medicinal or veterinary agent present therein may also be used as the optically anisotropic substance. That is, the medicinal or veterinary agent may be used in a dual role: as both the active agent in the tablet or bolus and as the optically anisotropic substance.

Suitable film coating agents for use in the highlighting coating suspension are mentioned above.

As aforesaid, the optically anisotropic substance has a minimum refractive index not greater than 2.00. The choice of this substance depends upon the film coating agent applied therewith, in that an optically anisotropic substance should be used which has a minimum refractive index which is the same as or similar to the refractive index of the film coating agent. It is an advantage to use an optically anisotropic substance which has a maximum refractive index which is as different as possible from its minimum refractive index, as this affords the best visual results. Details on typical materials which can be used are as follows:

| Film coating agents | Refractive index | |
|---|---|---|
| Methylcellulose | 1.50 | |
| Ethylcellulose | 1.47 | |
| Hydroxyethylcellulose | 1.51 | |
| Hydroxypropylcellulose | 1.56 | |
| Hydroxypropyl methylcellulose | 1.49 | |
| Sodium carboxymethylcellulose | 1.52 | |
| Cellulose acetate | 1.48 | |
| Shellac | 1.52 | |
| Acrylic resin | 1.48 | |
| Optically anisotropic substances | Refractive indices | |
| | Minimum | Maximum |
| Aluminium hydroxide | 1.50 | 1.56 |
| Kaolin | 1.56 | 1.57 |
| Talc | 1.54 | 1.59 |
| Calcium carbonate | 1.51 | 1.65 |
| Calcium sulphate | 1.57 | 1.61 |
| Barium carbonate | 1.53 | 1.68 |
| Magnesium carbonate | 1.51 | 1.70 |
| Cane sugar | 1.54 | 1.57 |
| α-Lactose | 1.52 | 1.57 |
| Tartaric acid | 1.50 | 1.61 |

The amount of optically anisotropic substance that is applied depends upon the degree of colour contrast required, the refractive indices of the substance, and its particle size. Thus, for example, in the case where the film coating agent is hydroxypropyl methylcellulose and the intagliated tablets used as starting material carry a film coat which is coloured with red or black iron oxide, the amounts of optically anisotropic substance which are used (expressed as % w/w of tablet weight) vary between 0.1 and 1.0%. In the case of corresponding tablets which carry a film coat coloured in more pastel shades, the said amounts vary between 0.5 and 5.0%. Approximately three times as much heavy magnesium carbonate, compared to light magnesium carbonate, is required to achieve the same effect.

The highlighting coating suspension used in Process A may optionally contain one or more film coating adjuvants which are conventional in the film coating art, for example plasticisers, for example glycerol, propylene glycol, polyethylene glycol, diethyl phthalate, glyceryl monostearate or castor oil, and surface active agents, for example polyoxyethylene sorbitan monooleate ['Tween' (Trade Mark) 80], and waxes, for example beeswax or carnauba wax. In addition, the said mixture may optionally contain at least one colouring agent, for example one or more of the specific colouring agents mentioned above. The net effect of this is that the colours in question [i.e. the colour of the main body of the article and the colour of the intagliation, on the one hand, and the colour of the highlighting coat, on the other] interact in a subtractive manner (see Encyclopaedia Britannica, Micropaedia, Volume III, 1974, 22). Numerous colour combinations are thus possible, the intagliation normally being seen as a pale version of the coloured highlighting coat. If the colour of the main body of the article and that of the highlighting coat are so-called complementary colours (see above reference), the main body of the article is seen as black and the intagliation is seen as a pastel colour (i.e. a pale version of the colour of the highlighting coat).

The highlighting coating suspension used in Process A may be an organic solvent-based suspension, for example where the solvent is a mixture of methylene dichloride and methanol, or it may be an aqueous suspension. When all of the ingredients are watersoluble, they should be applied in an organic solvent-based suspension.

The above outline of Process A applies mutatis mutandis to Process B except that in the latter case there is applied to the coloured intagliated articles a suspension containing at least one optically anisotropic substance having a minimum refractive index not greater than 2.00, but no film coating agent, in a suitable liquid. In the case where the coloured intagliated articles used as starting material have no film coating agent on their surface, or where they have a relatively water-soluble film coating agent, for example hydroxypropyl methylcellulose, on their surface, a suitable liquid is, for example, water or a mixture of a polyhalogenated (1-4C)alkane and a (1-4C)alkanol, for example a mixture of methylene dichloride and methanol. In the case where the said coloured intagliated articles have a relatively water-insoluble film coating agent, for example ethylcellulose, on their surface, a suitable liquid is an organic solvent, for example a polyhalogenated (1-4C)alkane, for example methylene dichloride, or a dialkyl ketone of not more than 6 carbon atoms, for example acetone. In the case where the liquid is water, at least one surface active agent, for example polyoxyethylene sorbitan monooleate ['Tween' (Trade Mark) 80], may optionally be present. In the case where the liquid is water or a mixture of a polyhalogenated (1-4C)alkane and a (1-

4C)alkanol, at least one humectant, for example glycerol, propylene glycol or a low molecular weight polyethylene glycol, for example polyethylene glycol 300, may optionally be present. In the case where the liquid is an organic solvent, there may optionally be present a plasticiser which is appropriate for the film coating agent in question, for example a di-(1-4C)alkyl phthalate, for example diethyl phthalate.

In a preferred embodiment of Process B the application of the above-mentioned suspension, containing at least one optically anisotropic substance having a minimum refractive index not greater than 2.00, is followed by the application in conventional manner of at least one film coating solution or suspension comprising at least one film coating agent, optionally at least one film coating adjuvant, and optionally at least one colouring agent.

The solvent used in the spray step (i.e. step 2) which characterises this invention depends upon the water-solubility of any film coating agent on the outer surface of the highlighted articles. If the film coating agent is relatively water-soluble, for example hydroxypropyl methylcellulose, or where there is no film coating agent on said outer surface, a suitable solvent is, for example:
  (a) water;
  (b) a mixture of water and a (1-4C)alkanol, for example methanol or ethanol;
  (c) a mixture of a polyhalogenated (1-4C)alkane, for example methylene dichloride, and a (1-4C)alkanol, for example methanol; or
  (d) a mixture of solvent (c) and a dialkyl ketone of not more than 6 carbon atoms, for example acetone.

The said solvent (a), (b), (c) or (d) may optionally contain at least one humectant, for example glycerol, propylene glycol or a low molecular weight polyethylene glycol, for example a polyethylene glycol having a molecular weight in the range 190 to 600, for example polyethylene glycol 300. It is surprising that, when a humectant is used, the highlighted products are not sticky or tacky at the end of the process.

In the case where the film coating agent on said outer surface is relatively insoluble in water, for example ethylcellulose, shellac or an acrylic resin, a suitable solvent is, for example:
  (e) a polyhalogenated (1-4C)alkane, for example methylene dichloride;
  (f) a dialkyl ketone of not more than 6 carbon atoms, for example acetone;
  (g) a mixture of solvents (e) and (f); or
  (h) a mixture of solvent (g) and a (1-4C)alkanol, for example methanol.

The said solvent (e), (f), (g) or (h) may optionally contain at least one plasticiser which is known in the art to be a suitable plasticiser for the film coating agent in question, for example a di-(1-4C)alkyl phthalate, for example diethyl phthalate or di-n-butyl phthalate, or an ester of glycerol with an alkanoic acid, for example glyceryl triacetate or glyceryl monostearate, or a vegetable oil, for example castor oil.

The spray step which characterises this invention is carried out under the conventional film coating conditions which are appropriate for the solvent in question and the film coating apparatus in question.

It is to be understood that, if desired, as a final step the highlighted products of this invention may be polished in conventional mannner using at least one wax, for example beeswax or carnauba wax, so as to impart an attractive appearance thereto.

The invention is illustrated but not limited by the following Examples:

EXAMPLE 1

A mixture of tablets, consisting of 10 kg. of white intagliated 10 mg. propranolol hydrochloride tablets (average weight 95 mg.) and 350 kg. of white intagliated placebo tablets (average weight 95 mg.), was treated as follows:

(a) Colour coating step

A clear coating solution was made up, which consisted of the following:

| | |
|---|---|
| hydroxypropyl methylcellulose ['Pharmacoat' (Trade Mark) 606, Shin-Etsu Chemical Company Ltd., Tokyo, Japan] | 8.4 kg. |
| glycerol | 1.68 kg. |
| deionized water | 63 l. |

9 liters of this clear coating solution were set aside for use in the highlighting step (see below). The following were added to the remainder of the clear coating solution:

| | |
|---|---|
| pink pigment dispersion ['Opaspray' (Trade Mark) M-1-1399B, Colorcon PLC, Orpington, Kent, England] | 5.4 kg. |
| deionized water | to 108 l. |

There was thus obtained a colour coating solution.

The above-mentioned mixture of tablets was film coated with the colour coating solution in a side-vented perforated drum coating machine (60 inch Accela-Cota) under the following conditions:

| | |
|---|---|
| inlet air temperature | 70–75° C. |
| outlet air temperature | 51–54° C. |
| process airflow | 4100 ft.$^3$ min.$^{-1}$ |
| chamber vacuum | −0.4" w.g. |
| spray rate | 660–700 ml. min$^{-1}$ |
| atomizing air pressure | 70–73 psi |
| drum speed | 4 r.p.m. for first hour, 4.5 r.p.m. for final 1.5 hours |

There was thus obtained a mixture of pink, film coated, intagliated tablets.

(b) Highlighting step

A highlighting coating suspension was prepared as follows:

Powdered light magnesium carbonate (1.296 kg.) was thoroughly dispersed in deionised water (9 l.). To the suspension were added the above-mentioned 9 l. of the clear coating solution [see section (a)], the resulting suspension was made up to 42 l. with deionised water, and then thoroughly mixed until homogeneous.

The above-mentioned mixture of pink, film coated, intagliated tablets was film coated with the highlighting coating suspension in the 60 inch Accela-Cota under the conditions described in section (a) except that the drum speed was 5 r.p.m. There was thus obtained a mixture of highlighted tablets.

(c) Solvent spray step

As soon as the highlighting step was completed, deionised water (20 l.) was sprayed on to the tablets under the same conditions as were used in the highlighting step. When all of the water had been applied, the drum was stopped and the tablets removed. There was thus obtained a mixture of highlighted tablets of excellent appearance.

EXAMPLE 2

(a) Highlighting step 10 kg. of a mixture of coloured film coated intagliated placebo and medicinal tablets (weight range 95–640 mg.) were heated to 60° C. in a side-vented perforated drum coating machine (24 inch Accela-Cota). One liter of a 3.3% w/v aqueous solution of hydroxypropyl methylcellulose ['Pharmacoat' (Trade Mark) 606], containing 0.65% w/v glycerol and light magnesium carbonate (30 g.) suspended therein, was applied continuously at 50 ml. min.$^{-1}$ by means of a low pressure airspray unit. The drum speed was kept at 16 r.p.m. and the temperature of the inlet air at 60° C. When all of the suspension had been applied, the drum was stopped and the tablets removed. There was thus obtained a mixture of coloured film coated tablets with intagliations highlighted in white.

(b) Solvent spray step

The mixture of highlighted tablets was heated to 60° C. in a side-vented perforated drum coating machine (24 inch Accela-Cota), and a 1% w/v aqueous solution of polyethylene glycol 300 (200 ml.) was applied continuously at 50 ml. min.$^{-1}$ by means of a low pressure air-spray unit. The drum speed was kept at 10 r.p.m. and the temperature of the inlet air at 60° C. When all of the solution had been applied, the drum was stopped and the tablets removed. There was thus obtained a mixture of highlighted tablets of excellent appearance.

EXAMPLE 3

(a)(i) Highlighting step 24,400 410 mg. pink film coated intagliated placebo tablets were heated to 60° C. in a side-vented perforated drum coating machine (24 inch Accela-Cota). One liter of a 3.3% w/v aqueous solution of hydroxypropyl methylcellulose ['Pharmacoat' (Trade Mark) 606], containing 0.65% w/v polyethylene glycol 300 and light magnesium carbonate (30 g.) suspended therein, was applied continuously at 50 ml. min.$^{-1}$ by means of a low pressure air-spray unit. The drum speed was kept at 16 r.p.m. and the temperature of the inlet drying air at 60° C. When all of the suspension had been applied, the drum was stopped and the tablets removed. There were thus obtained pink film coated tablets with intagliations highlighted in white.

(a)(ii) Highlighting step 37,000 270 mg. brown film coated intagliated placebo tablets were heated to 60° C. in a side-vented perforated drum coating machine (24 inch Accela-Cota). One liter of a 3.3% w/v aqueous solution of hydroxypropyl methylcellulose ['Pharmacoat' (Trade Mark) 606], containing 0.65% w/v polyethylene glycol 300, 0.1% w/v tartrazine water-soluble dye (Food, Drugs and Cosmetics Yellow No. 5), and light magnesium carbonate (30 g.) suspended therein, was applied continuously at 50 ml. min.$^{-1}$ by means of a low presure air-spray unit. The drum speed was kept at 16 r.p.m. and the temperature of the inlet drying air at 60° C. When all of the suspension had been applied, the drum was stopped and the tablets removed. There were thus obtained brown film coated tablets with intagliations highlighted in yellow.

(b) Solvent spray step 5 kg. of the pink highlighted tablets, obtained as described in (a) (i) above, and 5 kg. of the brown highlighted tablets, obtained as described in (a) (ii) above, were placed in a side-vented perforated drum coating machine (24 inch Accela-Cota) and heated to 60° C. 1:1 v/v methanol/methylene dichloride (2 l.) was applied continuously at 300 ml. min.$^{-1}$ by means of a high pressure airless spray unit. The drum speed was kept at 15 r.p.m. and the inlet air temperature at 60° C. When all of the solvent had been applied, the drum was stopped and the tablets removed. There were thus obtained highlighted tablets of excellent appearance.

EXAMPLE 4

The solvent spray step described in Example 3 was repeated except that the 2 l. of 1:1 v/v methanol/methylene dichloride were replaced by 1 l. of a 0.5% w/v solution of polyethylene glycol 300 in 1:1 v/v methanol/methylene dichloride. There were thus obtained highlighted tablets of excellent appearance.

EXAMPLE 5

(a) Colour coating step 50,000 200 mg. white intagliated medicinal tablets were heated to 60° C. in a side-vented perforated drum coating machine (24 inch Accela-Cota). 2.6 liters of a 9% w/v aqueous solution of hydroxypropyl methylcellulose ['Pharmacoat' (Trade Mark) 606], containing 1.4% w/v glycerol and pink pigment dispersion [175 g., 'Opaspray' (Trade Mark) pink, Colorcon PLC, Orpington, Kent, England], were applied continuously at 50 ml. min.$^{-1}$ by means of a low pressure air-spray unit. The drum speed was kept at 12 r.p.m. and the temperature of the inlet drying air at 60° C. When all of the suspension had been applied, the drum was stopped and the tablets removed. There were thus obtained pink film coated intagliated tablets.

(b) Highlighting step

The pink film coated intagliated tablets were heated to 60° C. in a side-vented perforated drum coating machine (24 inch Accela-Cota). 2 liters of a 1.5% w/v suspension of light magnesium carbonate in 1:1 v/v methanol/methylene dichloride were applied continuously at 300 ml. min.$^{-1}$ by means of a high pressure airless spray unit. The drum speed was kept at 15 r.p.m. and the temperature of the inlet air at 60° C. When all of the suspension had been applied, the drum was stopped and the tablets removed. There were thus obtained pink tablets having intagliations highlighted in white.

(c) Solvent spray step

The pink highlighted tablets were heated to 60° C. in a side-vented perforated drum coating machine (24 inch Accela-Cota). 1:1 v/v methanol/methylene dichloride (1 l.) was applied continuously at 300 ml. min.$^{-1}$ by means of a high pressure airless spray unit. The drum speed was kept at 15 r.p.m. and the inlet air temperature at 60° C. When all of the solvent had been applied, the drum was stopped and the tablets removed. There were thus obtained highlighted tablets of satisfactory appearance.

EXAMPLE 6

(a) Highlighting step 10 kg. of a mixture of coloured film coated intagliated placebo and medicinal tablets (weight range 100–640 mg.) were heated to 60° C. in a side-vented perforated drum coating machine (24 inch Accela-Cota). One liter of a 5% w/v aqueous solution of hydroxypropyl methylcellulose ['Pharmacoat' (Trade Mark) 606], containing 1% w/v polyethylene glycol 300 and light magnesium carbonate (30 g.) suspended therein, was applied continuously at 50 ml. min.$^{-1}$ by means of a low pressure air-spray unit. The drum speed was kept at 16 r.p.m. and the temperature of the inlet air at 60° C. When all of the suspension had been applied, the drum was stopped and the tablets removed. There was thus obtained a mixture of coloured film coated tablets with intagliations highlighted in white.

(b) Solvent spray step

Approximately 400 coloured film coated tablets with intagliations highlighted in white, obtained as described in (a) above, were added to approximately 52,000 190 mg. white placebo tablets. The mixture of tablets was heated at 60° C. in a side-vented perforated drum coating machine (24 inch Accela-Cota), and 500 ml. of a mixture of methanol and water (60:40 v/v) was applied continuously at 50 ml. min.$^{-1}$ using a low pressure air-spray unit. The drum speed was kept at 16 r.p.m. and the inlet air temperature at 60° C. When all of the solvent had been applied, the drum was stopped and the tablets removed. There were thus obtained highlighted tablets of satisfactory appearance.

EXAMPLE 7

The highlighting step and solvent-spray step described in Example 6 were repeated, except that in the latter step the 500 ml. of 60:40 v/v methanol/water were replaced by 1 l. of 70:30 v/v methanol/acetone. There were thus obtained highlighted tablets of satisfactory appearance.

What we claim is:

1. In a process for the manufacture of colored solid articles bearing at least one highlighted intagliation, which comprises:
   either (A) applying to colored intagliated articles, which themselves may be uncoated or film coated, a film coating suspension comprising at least one optically anisotropic substance having a minimum refractive index not greater than 2.00 and at least one film coating agent, the application being carried out in a conventional film coating apparatus in such a way that a rubbing action takes place between the articles being coated;
   or (B) applying to colored intagliated articles, which themselves may be uncoated or film coated, a suspension comprising at least one optically anisotropic substance having a minimum refractive index not greater than 2.00, but no film coating agent, and the application being carried out in a conventional film coating apparatus in such a way that a rubbing action takes place between the articles being coated; the improvement whereby better contrast is obtained between the highlighted intagliation and the rest of the surface of the article, said improvement comprising spraying the coloured solid articles bearing at least one highlighted intagliation obtained per (A) or (B) with a solvent in a conventional film coating apparatus in such a way that a rubbing action takes place between the said articles, whereby the contrast between the highlighted intagliation and the rest of the article surface is improved.

2. A process as claimed in claim 1 in which the coloured intagliated article is a pharmaceutical or veterinary unit dosage form or a piece of sugar confectionery having approximately the same dimensions as a pharmaceutical tablet.

3. A process as claimed in claim 2 in which the pharmaceutical or veterinary unit dosage form is a pharmaceutical or veterinary tablet.

4. A process as claimed in claim 1 in which the said coloured solid articles bearing at least one highlighted intagliation either have no film coating agent on their outer surface or they have a relatively water-soluble film coating agent on their outer surface, and in which the said solvent used in step (2) is (a) water, (b) a mixture of water and a (1-4C)alkanol, (c) a mixture of a polyhalogenated (1-4C)alkane and a (1-4C)alkanol, or (d) a mixture of solvent (c) and a dialkyl ketone of not more than 6 carbon atoms.

5. A process as claimed in claim 4 in which the said solvent contains at least one humectant.

6. A process as claimed in claim 5 in which the humectant is glycerol, propylene glycol, or a low molecular weight polyethylene glycol.

7. A process as claimed in claim 4 in which the solvent is water.

8. A process as claimed in claim 1 in which the said coloured solid articles bearing at least one highlighted intagliation have a relatively water-insoluble film coating agent on their outer surface, and in which the said solvent used in step (2) is (e) a polyhalogenated (1-4C)alkane, (f) a dialkyl ketone of not more than 6 carbon atoms, (g) a mixture of solvents (e) and (f), or (h) a mixture of solvent (g) and a (1-4C)alkanol.

9. A process as claimed in claim 8 in which the said solvent contains at least one plasticiser which is suitable for the said relatively water-insoluble film coating agent.

10. A process as claimed in claim 9 in which the plasticiser is a di-(1-4C)alkyl phthalate, an ester of glycerol with an alkanoic acid, or a vegetable oil.

* * * * *